United States Patent
Leight

[11] Patent Number: 5,979,451
[45] Date of Patent: Nov. 9, 1999

[54] EARMUFF SOUND PROTECTOR

[75] Inventor: Howard S. Leight, Malibu, Calif.

[73] Assignee: Howard S. Leight and Associates, Inc., San Diego, Calif.

[21] Appl. No.: 07/451,199

[22] Filed: Dec. 15, 1989

Related U.S. Application Data

[60] Division of application No. 07/225,049, Jul. 27, 1988, abandoned, which is a continuation-in-part of application No. 07/036,118, Apr. 9, 1987, Pat. No. 4,774,938, and application No. 07/064,173, Jun. 18, 1987, Pat. No. 4,819,624.

[51] Int. Cl.⁶ .................................................... A61F 11/00
[52] U.S. Cl. ............................................ 128/864; 128/866
[58] Field of Search ..................................... 128/864, 865, 128/866, 867, 868, 857

[56] References Cited

U.S. PATENT DOCUMENTS

| | | | |
|---|---|---|---|
| 2,437,049 | 3/1948 | Salisbury | 128/866 |
| 2,670,737 | 3/1954 | Cantor | 128/864 |
| 2,858,544 | 11/1958 | Roth | 128/866 |
| 2,883,671 | 4/1959 | Hornickel | 128/866 |
| 3,408,658 | 11/1968 | Beguin | 128/866 |
| 3,661,225 | 5/1972 | Anderson | 128/866 |
| 3,872,559 | 3/1975 | Leight | 128/864 |
| 3,944,018 | 3/1976 | Satory | 128/866 |
| 4,253,452 | 3/1981 | Powers | 128/864 |
| 4,437,538 | 3/1984 | Ohlsson | 128/867 |
| 4,774,938 | 10/1988 | Leight | 128/864 |

*Primary Examiner*—Michael A. Brown
*Attorney, Agent, or Firm*—Arthur Freilich; Leon Rosen; Robert Hornbaker

[57] ABSTRACT

An earplug of the slow recovery type is described, which has open cells for expelling gas to the outside during compression, but which resists the entry of water through the outside and the soiling of the outside by dirt. The earplug includes a body formed of pressure-molded slow recovery resilient foam material forming multiple gas-filled shells. The plug body has a surface region forming a skin wherein the average cell cross-sectional area is less than half that of cells at the center of the body, and is less than one-tenth millimeter, the surface region being primarily continuous.

2 Claims, 2 Drawing Sheets

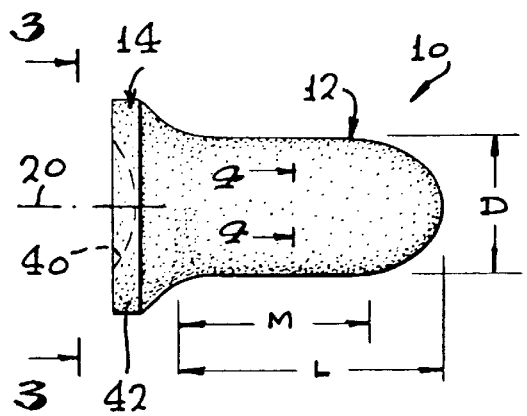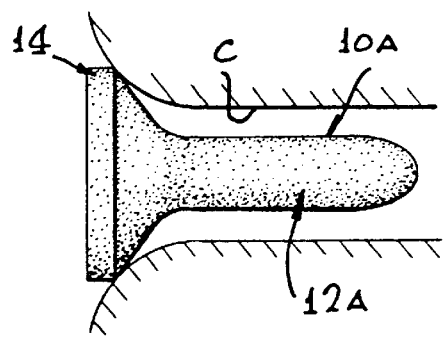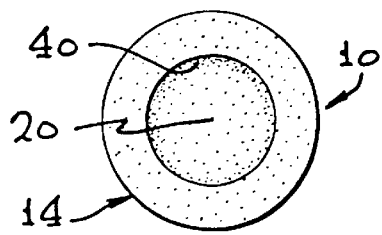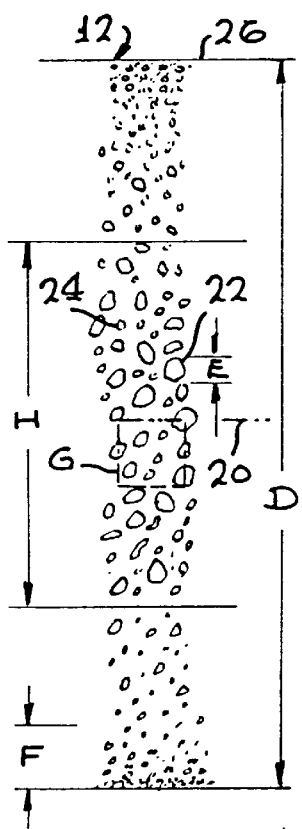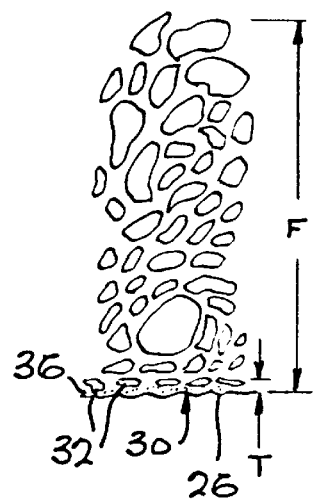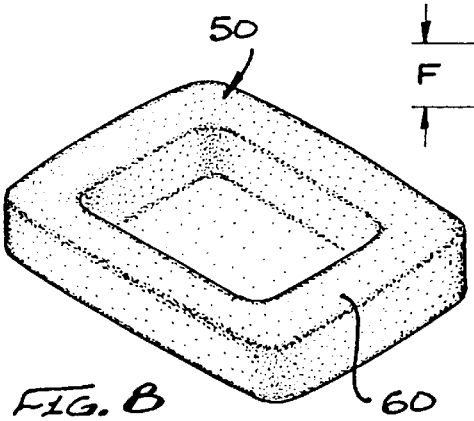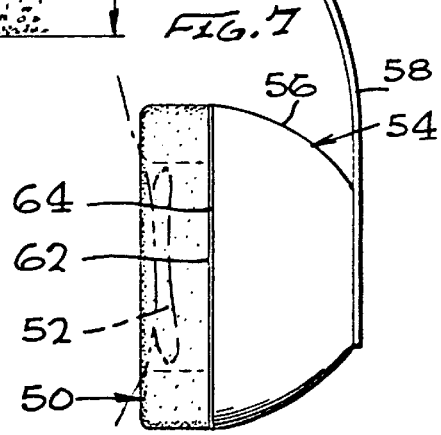

EARMUFF SOUND PROTECTOR

CROSS-REFERENCE TO RELATED PATENT

This application is a division of Ser. No. 07/225,049 filed Jul. 27, 1988 now abandoned which is a continuation-in-part of Ser. No. 36,118 filed Apr. 9, 1987, now U.S. Pat. No. 4,774,938 and a continuation-in-part of Ser. No. 64,173 filed Jun. 18, 1987 now U.S. Pat. No. 4,819,624.

BACKGROUND OF THE INVENTION

Slow recovery earplugs, such as the type described in U.S. Pat. No. Reissue 29,487 have gained wide acceptance. Such earplugs can be rolled in the fingers to a small diameter, inserted into the ear, and allowed to expand over a period of between a few seconds to a few minutes to completely fill the end of the user's ear canal. Such earplugs have been previously formed by punching cylinders out of a thick sheet of slow recovery material, which is generally an open cell foam that allows air to escape when squeezing the earplug before insertion. Such earplugs easily pick up water or other fluids which hamper their use. Also, the multiple cut cells at the surface tend to pick up dirt, especially when a worker with dirty hands rolls the earplug between his fingers to compress it prior to insertion. A slow recovery earplug which resisted soiling and the pickup of water at its surface would be more sanitary and have a longer lifetime of use.

SUMMARY OF THE INVENTION

In accordance with one embodiment of the present invention, a slow recovery earplug is provided, which resists soiling especially during squeezing of the earplug to fit into the ear. The earplug includes a main body formed of pressure-molded slow recovery resilient foam plastic material that forms multiple gas-filled shells. The earplug has a surface region which forms an integral pressure-molded skin that is largely impervious to solid and liquid contaminants. The same construction is useful in an earmuff and a band earplug.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side elevation view of an earplug constructed in accordance with the present invention, shown in its fully expanded condition.

FIG. 2 is a view similar to that of FIG. 1, but showing the earplug in its fully compressed condition.

FIG. 3 is a view taken on the line 3—3 of FIG. 1.

FIG. 4 is an enlarged view of a section of the earplug of FIG. 1, taken on the line 4—4 of FIG. 1.

FIG. 5 is an enlarged view of a portion of the surface of the earplug of FIG. 1.

FIG. 6 is an enlarged view of a portion of the earplug section of FIG. 4, near the surface of the earplug.

FIG. 7 is a partial side view of an earmuff constructed in accordance with another embodiment of the invention.

FIG. 8 is a perspective view of the earmuff portion of FIG. 7.

DESCRIPTION OF THE PREFERRED EMBODIMENTS

Figure 9:
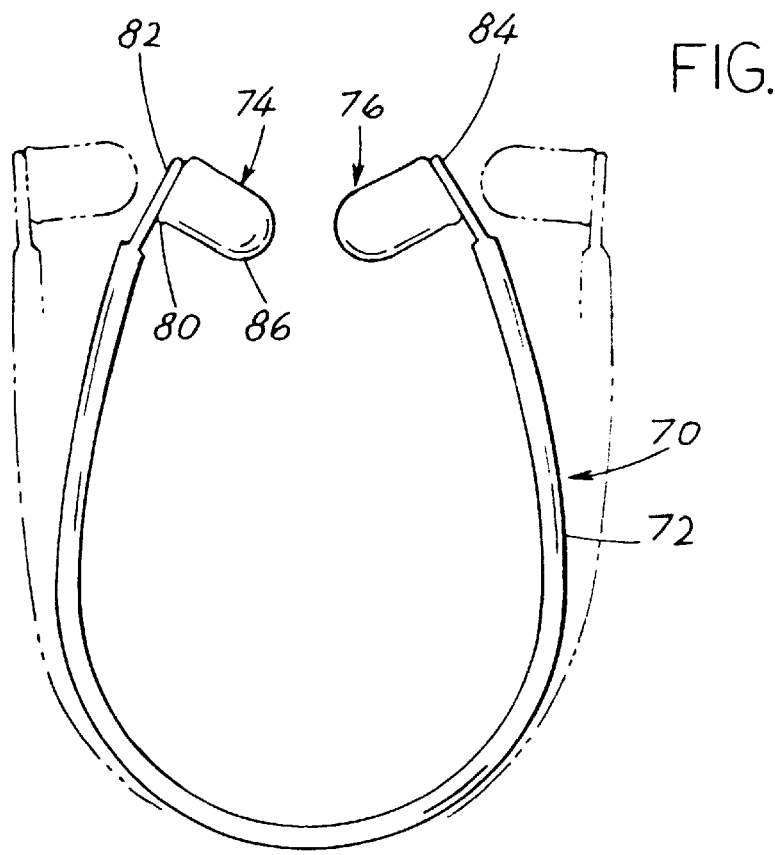
FIG. 9 is a plan view of a band earplug constructed in accordance with another embodiment of the invention, showing in phantom lines, the configuration of the band after it is expanded to fit a person.

FIG. 1 illustrates a slow recovery earplug 10 which includes a largely bullet-shaped main body portion 12 and a flared rear end 14. As indicated in FIG. 2, the main body portion is designed to be compressed to the configuration shown at 12A (FIG. 2) so it can be inserted into the ear canal C of a person. During a period of about one minute, the earplug expands to near its uncompressed configuration, and presses against the walls of the ear canal to block noise. As the main body portion of a slow recovery earplug is rolled in the fingers to compress it, liquid and solid foreign materials which may lie on the worker's fingers could be picked up by the earplug. The earplug is formed generally of an open cell material to enable the escape of air while the body portion is being compressed. In prior slow recovery earplugs, which were punched out of thick sheets of slow recovery material, large open cells were present at the surface of the earplug. Such large open cells easily absorb foreign material, so that the earplug could quickly become soiled, and could become damaged if it came in contact with water or other liquids.

The present earplug 10 is pressure molded from a slow recovery urethane foam material. This is accomplished by mixing the foam materials, placing them in a mold having a cavity of the shape shown in FIG. 1, and closing the mold, with a very small opening for escape of air such as a slit of about 0.2 millimeters width. It is also possible to inject the material into a substantially closed mold. The amount of foamable material is sufficient to fill a cavity of a volume greater than that of the finished earplug, so the material expands to the full size of the cavity and then presses with considerable pressure against the walls of the cavity. Sufficient foamable material is present that the pressure of the expanding foam against the mold walls is at least about 0.5 psi; applicant uses about 2 psi for the examples of earplugs described herein. For lower pressures, such as those approaching zero pressure (the top of the mold is open) the cells near the skin are large, and can more easily pick up moisture and dirt.

The appearance of the surface of an earplug molded in an open mold is not as smooth as for the pressure-molded earplug. Applicant finds that the size of the gas-filled cells within the pressure-molded earplug is greatest at the center of the earplug, and decreases at locations progressively closer to the surface of the earplug. Applicant's pressure-molded earplug forms an integral skin at the surface where the pores are very small, and with most of the skin area being substantially closed. The size of the gas-filled cells is greatest at the center of the earplug, with many cells thereat being more than 0.1 millimeter in diameter, and the cross-sectional area of the cells is less at the skin. The skin results in a stiffer earplug when it has been rolled to a small diameter, which makes it easier to insert the earplug into the ear canal. The skin forms few openings that can pick up and retain liquid and soiling material. Thus, such foreign material tends not to be absorbed into the earplug, so that the earplug's surface tends to remain clean and the lifetime of use of the earplug is longer than those of the prior art described above.

FIG. 4 illustrates a portion of a cross section of the earplug main body portion 12 of FIG. 1. The earplug main body portion 12 has a substantially cylindrical outer surface (it could be a polygon and/or have a small taper) and has a diameter D of about 11 mm (millimeters) along most of its length and is formed of multiple gas-filled cells that each has a width of a plurality of thousandths of an inch. Near the center or axis 20, the earplug includes numerous large cells 22 of a diameter E of at least 0.2 mm. A plurality of such large cells lie in each square millimeter G of a majority of the cross-sectional area of the earplug at the middle H (which is one-half D). Small cells 24 of an average diameter less than 0.2 mm lie interspersed with the large cells. The cross-sectional area occupied by large cells of over 0.2 mm diameter decreases at locations progressively closer to the surface 26 of the earplug. Within a distance F of one millimeter from the earplug surface, there are twice as many cells, which are small, in each square millimeter of cross-sectional area than at the middle region of height H. The average cross-sectional area of the cells within one-half millimeter of the surface is less than half the average cross-sectional area of cells within the central 5 mm of the main body portion. The decrease in cell size near the surface results in resistance to the soiling of the earplug. It is also found that the pressure-molded earplug develops a skin 30 (FIG. 6) of a thickness T of about 0.05 mm, with most cells 32 nearest the skin being of about 0.05 to 0.1 mm diameter and spaced about 0.05 mm from the outside or surface 26 to form the skin 30 between those cells 32 and the surface 26. As shown in FIG. 5 which shows a view of the skin from the outside, the skin includes numerous shallow recesses 34, and with only a limited number of holes through which air can escape and through which liquids and dirt can be absorbed into the earplug.

The skin also includes talcum powder 36 embedded therein, which is produced by coating the mold surface with talcum powder before pouring in the foam material. Applicant finds that the outside of the earplug has a relatively low friction against the skin, which facilitates its removal from the ear, and is substantially smooth and rejects the intrusion of dirt therein.

The flanged or flared rear end 14 of the earplug limits the depth of insertion of the earplug into the ear, and also provides a region to be grasped to remove the earplug from the ear canal. Because of the flange, users tend to roll only the bullet-shaped or largely cylindrical body 12, while leaving the-flanged end 14 at its full size. This reduces the possibility of deep insertion of the compressed earplug into the ear, and it reduces the difficulty of removing the earplug. The main body portion of length L is of substantially uniform width (±10% of the width D at the middle) along a distance M which is most of the length of the main portion. To facilitate grasping of the flanged rear end, applicant includes a recess 40 in the rear of the earplug along the axis 20 to provide a thinner outer region 42 to facilitate grasping of this region to pull out the earplug The recess 40 also avoids bulging of the rear end when the main body portion is compressed, such bulging resisting full insertion of the main body portion in the ear canal.

FIGS. 7 and 8 illustrate another ear sound-blocking member in the form of an earmuff portion or earmuff 50, which is formed of the same pressure-molded slow recovery resilient foam plastic material as the earplug described above. The earmuff 50 comprises at least a portion extending in a closed loop of a width and length that are each of a plurality of centimeters, and which can extend around the ear 52 of the wearer. The earmuff 50 is designed to be held on a band device 54 which includes a mount 56 held by a band 58 that extends halfway around a person's head and which resiliently holds a pair of earmuffs against the regions of a person's head around his ears. The slow recovery material slowly adjusts well to the contours of the particular wearer to effectively block sound. The use of pressure-molded slow recovery material results the surface 60 of the earmuff resisting the pickup of moisture and dirt, which could result in a less sanitary earplug and one with a shorter lifetime of use.

The earmuff 50, like the earplug described above, is of urethane foam that is molded in a closed mold, which has only a small thin opening for the escape of air from the mold while substantially preventing the escape of foaming plastic. The urethane foam is kept in the mold at a pressure of at least 0.5 psi, and preferably about 2 psi. However, even minimal pressure in molding of slow recovery material can create a skin with a much smoother surface than is created by merely punching earplugs out of a sheet of slow recovery material. The particular earmuff 50 is designed to be mounted by adhesive tape 62 on a surface 64 of the mount.

Figure 10:
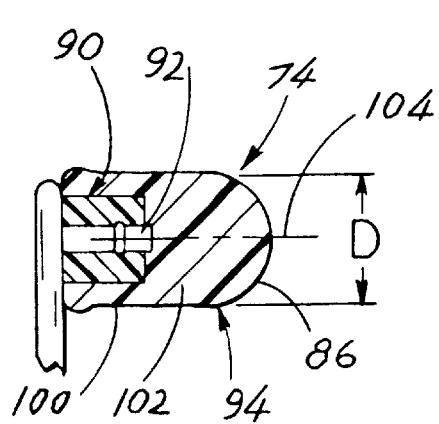
FIG. 10 is a sectional view of an earplug device of the band earplug of FIG. 9.
Figure 11:
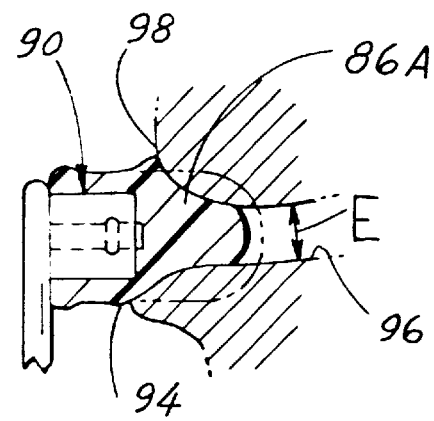
FIG. 11 is a view similar to that of FIG. 10, but showing the earplug device after placement against an ear.

FIGS. 9–11 illustrate another sound-blocking apparatus in the form of a band earplug 70 which includes a band 72 and a pair of earplug devices 74, 76. Each earplug device has a rearward portion 80 located at an end 82 or 84 of the band, and a forward portion 86 which is pressed toward the ear of a wearer. Each earplug device such as 74 includes an armature 90 of resilient foam of medium resilience mounted on a post 92 of the band end, and an earplug body 94 of a softer foam mounted on the armature.

The earplug body 94 is of a diameter D such as 13 mm which is considerably larger than the diameter E of a human ear canal 96 which is about 7 mm in diameter. The forward portion 86 of the earplug device and of the earplug body is pressed against the walls 98 that surround the entrance of the ear canal. The forward portion 86A of the body is firmly seated against the entrance to the ear canal.

The earplug body 94 is formed of a pressure molded slow recovery resilient foam plastic material such as a urethane. The molding is accomplished by flowing the liquid foamable material into a substantially closed mold, and allowing the foam to expand and fill the mold. Even a small pressure of the foamable material against the walls of the mold results in a skin at the surface of the earplug body which is smoother than the surface of a slow recovery material earplug formed by punching an earplug out of a sheet of material as in U.S. Pat. No. Reissue 29,489 or by dip molding as in U.S. Pat. No. 4,490,857. A molding pressure of at least about 0.5 psi is preferred.

The earplug body includes a thin rearward part 106 that surrounds the armature and a much thicker forward part 102 that lies in front of the armature along the body axis 104.

Thus, the invention provides an ear sound-blocking member which is an earplug that fits in or against the outside of the ear canal or an earmuff, of slow recovery material, which resists soiling or absorption of liquid therein and which can facilitate insertion of an earplug into the ear canal. The member includes a pressure-molded slow recovery resilient foam plastic material which forms multiple gas-filled cells, and which has been formed in a closed mold at a pressure that is preferably at least 0.5 psi. The member forms a smooth skin, and is preferably primarily closed in that there are compressed small cells spaced from the outside to form a generally solid (generally unperforated by visible cells) skin between such elongated small cells and the outside of the member. The earplug has a flared rear end that tends not to be compressed by persons, and which therefore helps avoid too deep insertion into the ear canal.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for forming an earmuff device comprising:

molding a pair of earmuffs of a shape and size so each can extend in a closed loop around a person's ear, and mounting each earmuff on a band that can extend about halfway around a person's head to hold the earmuffs around the person's ears;

said step of molding including placing open cell foamable slow recover material in a substantially closed mold and expanding the material to fill the mold, with the amount of material being sufficient that the earmuff is molded at a pressure of at least about 0.5 pounds per square inch.

2. An earmuff device comprising:

a band which is constructed to extend about halfway around a person's head, and which has opposite ends;

a pair of earmuffs mounted on said opposite ends of said band, said band resiliently pressing said earmuffs towards the opposite sides of the person's head, each earmuff including a portion extending in a closed loop of a size to extend around the ear of the person and formed of pressure-molded slow recovery resilient foam plastic material, with each earmuff having an integral pressure-molded skin;

said foam plastic material comprises multiple cells, with the average cross-sectional area of cells at the surface of said earmuff being less than at the middle of the earmuff.

* * * * *